United States Patent
Huang et al.

(10) Patent No.: US 12,178,654 B2
(45) Date of Patent: Dec. 31, 2024

(54) ULTRASONIC IMAGING OF ACOUSTIC ATTENUATION COEFFICIENTS WITH ELEVATION COMPOUNDING

(71) Applicant: KONINKLIJKE PHILIPS N.V., Eindhoven (NL)

(72) Inventors: Sheng-Wen Huang, Ossining, NY (US); Hua Xie, Cambridge, MA (US); Man Nguyen, Melrose, MA (US); Jean-luc Francois-Marie Robert, Cambridge, MA (US); William Tao Shi, Wakefield, MA (US); Carolina Amador Carrascal, Everett, MA (US); Vijay Thakur Shamdasani, Kenmore, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 274 days.

(21) Appl. No.: 17/630,401

(22) PCT Filed: Jul. 29, 2020

(86) PCT No.: PCT/EP2020/071413
§ 371 (c)(1),
(2) Date: Jan. 26, 2022

(87) PCT Pub. No.: WO2021/018968
PCT Pub. Date: Feb. 4, 2021

(65) Prior Publication Data
US 2022/0280138 A1 Sep. 8, 2022

Related U.S. Application Data

(60) Provisional application No. 62/880,282, filed on Jul. 30, 2019.

(51) Int. Cl.
*A61B 8/08* (2006.01)
*G01S 7/52* (2006.01)
*G01S 15/89* (2006.01)

(52) U.S. Cl.
CPC ............ *A61B 8/5207* (2013.01); *A61B 8/085* (2013.01); *A61B 8/5223* (2013.01); *G01S 7/52036* (2013.01); *G01S 15/8925* (2013.01)

(58) Field of Classification Search
CPC ..... A61B 8/5207; A61B 8/085; A61B 8/5223; G01S 7/52036; G01S 15/8925
See application file for complete search history.

(56) References Cited

U.S. PATENT DOCUMENTS

| 5,482,045 A | 1/1996 | Rust et al. |
| 5,671,746 A | 9/1997 | Dreschel et al. |
(Continued)

FOREIGN PATENT DOCUMENTS

WO 2004093671 A1 11/2004

OTHER PUBLICATIONS

International Search Report and Written Opinion for the PCT/EP2020/071413; Mailing date: Oct. 30, 2020, 12 pages.
(Continued)

*Primary Examiner* — Chao Sheng (57) ABSTRACT

An ultrasound system produces maps of acoustic attenuation coefficients from B mode image signals. A plurality of maps located in different parallel and elevationally separated planes (A, B, C, D, E) are produced, then compounded in the elevation direction. Confidence maps may also be produced for one or more attenuation coefficient maps, and the confidence map displayed or its measures used to determine weighting for the compounding process. The compounding of elevationally separate planes improves attenuation coef-
(Continued)

ficient estimation in the presence of blood vessels affecting the estimates in one or more of the planes.

18 Claims, 5 Drawing Sheets

(56) References Cited

U.S. PATENT DOCUMENTS

| | | |
|---|---|---|
| 5,833,613 A | 11/1998 | Averkiou et al. |
| 5,997,479 A | 12/1999 | Savord et al. |
| 6,013,032 A | 1/2000 | Savord |
| 6,511,426 B1 | 1/2003 | Hossack et al. |
| 6,530,885 B1 | 3/2003 | Entrekin et al. |
| 6,623,432 B2 | 9/2003 | Powers et al. |
| 8,137,272 B2 | 3/2012 | Cooley et al. |
| 2004/0054285 A1 | 3/2004 | Freiburger et al. |
| 2004/0243001 A1* | 12/2004 | Zagzebski .......... G01S 15/8995 600/437 |
| 2013/0012819 A1 | 1/2013 | Haugen et al. |
| 2013/0281859 A1 | 10/2013 | Lause |
| 2015/0119701 A1 | 4/2015 | Vignon et al. |
| 2017/0258438 A1 | 9/2017 | Kanayama |
| 2020/0214666 A1* | 7/2020 | McLaughlin ....... G01S 7/52046 |

OTHER PUBLICATIONS

Liu, W. et al, "Acoustic backscatter and effective scatterer size estimates using a 2D CMUT transducer", Phys. Med. Biol. 2008, vol. 53, pp. 4169-4183.

Walach E. et al., "Local tissue attenuation images based on pulsed-echo ultrasound scans", IEEE Trans Biomed Eng., 1989, 36(2), pp. 211-221.

\* cited by examiner

ULTRASONIC IMAGING OF ACOUSTIC ATTENUATION COEFFICIENTS WITH ELEVATION COMPOUNDING

CROSS-REFERENCE TO PRIOR APPLICATIONS

This application is the U.S. National Phase application under 35 U.S.C. § 371 of International Application No. PCT/EP2020/071413, filed on Jul. 29, 2020, which claims the benefit of U.S. Provisional Patent Application No. 62/880,282, filed on Jul. 30, 2019. These applications are hereby incorporated by reference herein.

This invention relates to ultrasound imaging systems and, in particular, to the imaging of acoustic attenuation coefficient maps with 1.75D and 2D array transducers.

Pulse-echo ultrasound imaging systems transmit beams of acoustic energy over an image field. As each transmitted beam encounters acoustic reflectors and tissue boundaries, some of the transmitted energy is reflected back to the transmitting transducer and received as an echo. In this way, a sequence of echoes is received from progressively deeper tissues as the ultrasound beam energy travels deeper into the body. The amplitudes of the echoes are detected and displayed in correspondence with their times of reception, which correspond to the depths from which they were received. The display thereby reveals characteristics of the structure of the tissue within the body. But the beam energy is continually attenuated as it travels through the tissue and encounters acoustic absorption and scattering along the paths of the beams. This attenuation will result in the reception of generally stronger echoes from tissue in the near field, and generally weaker echoes from tissue at greater depths. Without compensation for this effect, the resulting image will appear brighter in the near field (from higher amplitude echoes) and darker in the far field due to the reception of lower echo amplitudes. The common compensation for this effect is time gain control (TGC), whereby the receiver increases the amplification of echo signals as they are received from progressively greater depths. Ultrasound systems are equipped with TGC settings which enable the user to select the gain applied at different depths, from which the ultrasound system computes a TGC curve for continual gain variation during echo reception. Ultrasound systems are also commonly equipped with pre-determined TGC curves which experience has shown are typical for various tissue types. Thus, a user can call up a pre-computed TGC curve for the liver for an abdominal exam, or a different pre-computed TGC curve when imaging the breast. The typical curves are exactly that, since the attenuation characteristics of tissue differ from one person to another by reason of tissue density variation, composition, location differences, and other properties. It would thus be desirable to know the attenuation characteristics of the specific tissue being diagnosed, rather than rely upon a typical or average characteristic. Accordingly, efforts have been directed toward measuring the attenuation characteristics for a subject in vivo by estimating and displaying the degree of attenuation for each point in an ultrasound image field. See, e.g., "Local Tissue Attenuation Images Based on Pulsed-Echo Ultrasonic Scans" by Walach et al., *IEEE Trans. On Biomedical Engineering*, vol. BME-33, no. 7, July 1986 at pp 637-43. Walach et al. propose that such maps of local attenuation in an image field can be used to pinpoint tissue pathology by reason of its different attenuation characteristic from that of healthy tissue. An example of this property is the diagnosis of fatty liver disease. As fat is more attenuative than normal liver tissue, the acoustic attenuation characteristic can potentially be used to stage fatty liver disease.

The estimations used to produce such attenuation maps, however, are generally dependent upon certain assumptions made concerning tissue, such as the local homogeneity of tissue, which may not be the case throughout the image field. Tissue such as liver tissue contains networks of blood vessels throughout the parenchyma. The presence of vasculature adjacent to an image plane, which would not be visible in the image, can affect acoustic attenuation estimation in the image plane. Other sources of error include the effects of frequency-dependent acoustic diffraction due to aberration, speckle, aperture obstruction, clutter, or other adverse conditions. It would be desirable to produce maps of acoustic attenuation in an image field which are less subject to such error sources.

In accordance with the principles of the present invention, an ultrasound imaging system, method, and technique are described for more accurately estimating acoustic attenuation coefficients over an ultrasound image field. Instead of acquiring echo signal data only in the plane of interest, echo signals for acoustic attenuation estimation are acquired from a plurality planes differing in elevation. Echo signal data is thus acquired adjacent to the primary plane of interest. The acoustic attenuation estimates from the plurality of planes is compounded, thereby diminishing the effect of inaccurate in-plane estimates. In accordance with a further aspect of the present invention, data points which are less accurate or reliable can be deleted from compounding, or weighted less when combined with the other elevationally-varying values.

Figure 1:
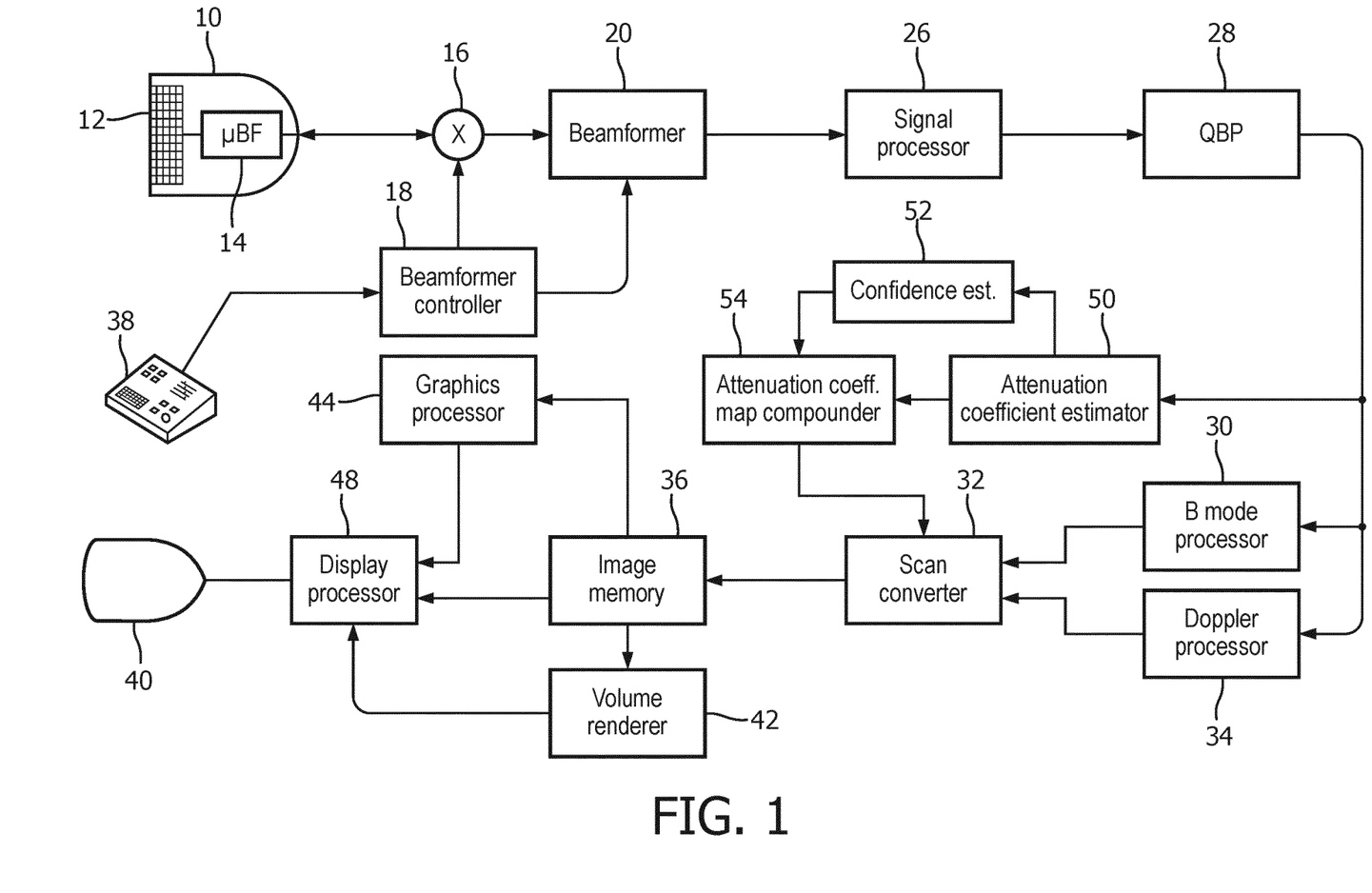
FIG. 1 illustrates in block diagram form an ultrasound system configured in accordance with the principles of the present invention.

Referring to FIG. 1, an ultrasonic diagnostic imaging system constructed in accordance with the principles of the present invention is shown in block diagram form. A transducer array 12 is provided in an ultrasound probe 10 for transmitting ultrasonic waves and receiving echo information. The transducer array 12 may be a one- or two-dimensional array of transducer elements capable of scanning in two or three dimensions, for instance, in both elevation (in 3D) and azimuth. A preferred transducer array for scanning in accordance with the present invention is a 1.75D array with limited beam steering in elevation, or a 2D array with full electronic steering capability in both elevation and azimuth. The transducer array 12 is coupled to a microbeamformer 14 in the probe which controls transmission and reception of signals by the array elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled by the probe cable to a transmit/receive (T/R) switch 16 which switches between transmission and reception and protects the main beamformer 20 from high energy transmit signals. The transmission of ultrasonic beams from the transducer array 12 under control of the microbeamformer 14 is directed by a beamformer controller 18 coupled to the T/R switch and the main beamformer 20, which receives input from the user's operation of the user interface or control panel 38. Among the transmit characteristics controlled by the transmit controller are the number, spacing, amplitude, phase, frequency, polarity, and diversity of transmit waveforms. Beams formed in the direction of pulse transmission may be steered straight ahead from the transducer array, or at different angles on either side of an unsteered beam for a wider sector field of view. For some applications, unfocused plane waves may be used for transmission. Most 1D array probes of relatively small array length, e.g., a 128-element array, do not use a microbeamformer but are driven and respond directly to the main beamformer.

The echoes received by a contiguous group of transducer elements are beamformed by appropriately delaying them and then combining them. The partially beamformed signals produced by the microbeamformer 14 from each patch are coupled to the main beamformer 20 where partially beamformed signals from individual patches of transducer elements are combined into a fully beamformed coherent echo signal. For example, the main beamformer 20 may have 128 channels, each of which receives a partially beamformed signal from a patch of 12 transducer elements. In this way the signals received by over 1500 transducer elements of a two-dimensional array transducer can contribute efficiently to a single beamformed signal, and signals received from an image plane are combined.

The microbeamformer 14 or the beamformer 20 also include amplifiers which amplify the signals received from each element or patch of the transducer array 12. These amplifiers have controllable gain characteristics, which are controlled by a TCG curve stored in the ultrasound system, TGC controls on the user interface 38, or a combination of both. See, e.g., U.S. Pat. No. 5,482,045 (Rust et al.) Beamformation by delaying and summing signals from individual transducer elements or patches is thus performed with echo signals that have undergone time gain control compensation.

The coherent echo signals undergo signal processing by a signal processor 26, which includes filtering by a digital filter and noise or speckle reduction as by spatial or frequency compounding. The filtered echo signals are coupled to a quadrature bandpass filter (QBP) 28. The QBP performs three functions: band limiting the RF echo signal data, producing in-phase and quadrature pairs (I and Q) of echo signal data, and decimating the digital sample rate. The QBP comprises two separate filters, one producing in-phase samples and the other producing quadrature samples, with each filter being formed by a plurality of multiplier-accumulators (MACS) implementing an FIR filter. The signal processor can also shift the frequency band to a lower or baseband frequency range, as can the QBP. The digital filter of the signal processor 26 can be a filter of the type disclosed in U.S. Pat. No. 5,833,613 (Averkiou et al.), for example.

The beamformed and processed coherent echo signals are coupled to a B mode processor 30 which produces signals for a B mode image of structure in the body such as tissue. The B mode processor performs amplitude (envelope) detection of quadrature demodulated I and Q signal components by calculating the echo signal amplitude in the form of $(I^2+Q^2)^{1/2}$. The quadrature echo signal components are also coupled to a Doppler processor 34. The Doppler processor 34 stores ensembles of echo signals from discrete points in an image field which are then used to estimate the Doppler shift at points in the image with a fast Fourier transform (FFT) processor. The rate at which the ensembles are acquired determines the velocity range of motion that the system can accurately measure and depict in an image. The Doppler shift is proportional to motion at points in the image field, e.g., blood flow and tissue motion. For a color Doppler image, the estimated Doppler flow values at each point in a blood vessel are wall filtered and converted to color values using a look-up table. The wall filter has an adjustable cutoff frequency above or below which motion will be rejected such as the low frequency motion of the wall of a blood vessel when imaging flowing blood. The B mode image signals and the Doppler flow values are coupled to a scan converter 32 which converts the B mode and Doppler samples from their acquired R-θ coordinates to Cartesian (x,y) coordinates for display in a desired display format, e.g., a rectilinear display format or a sector display format. Either the B mode image or the Doppler image may be displayed alone, or the two shown together in anatomical registration in which the color Doppler overlay shows the blood flow in tissue and vessels in the image. Another display possibility is to display side-by-side images of the same anatomy which have been processed differently or, in the case of multi-plane acquisition, images of different planes. This display format is useful when comparing images.

The scan converted image is coupled to an image data memory 36, where it is stored in memory locations addressable in accordance with the spatial locations from which the image values were acquired. Image data from 3D scanning can be accessed by a volume renderer 42, which converts the echo signals of a 3D data set into a projected 3D image as viewed from a given reference point as described in U.S. Pat. No. 6,530,885 (Entrekin et al.) The 3D images produced by the volume renderer 42 and 2D images produced by the scan converter 32 are coupled to a display processor 48 for further enhancement, buffering and temporary storage for display on an image display 40.

In accordance with the principles of the present invention, the ultrasound system of FIG. 1 includes a subsystem which produces image maps of acoustic attenuation coefficient estimates. The subsystem includes an attenuation coefficient estimator 50, which receives B mode echo signals, preferably from the QBP 28 prior to detection. The attenuation coefficient estimator is capable of producing an attenuation coefficient map from echo signals acquired from a scan plane and, in accordance with the present invention, a plurality of attenuation coefficient maps from a plurality of scan planes separated in the elevation dimension, as described more fully in the subsequent drawings and description. The attenuation coefficient estimator 50 operates on the tissue values of I, Q data prior to detection of pixel values of a B mode image, and processes the tissue values in conjunction with a map of reference values, such as attenuation coefficient measurements made of a homogeneous tissue phantom, a theoretical model of attenuation coefficients, or a numerical simulation of attenuation coefficients. Various reference value maps are stored in the attenuation coefficient estimator 50 or in a memory accessible by the attenuation coefficient estimator 50. Depending on the transmit/receive acoustic settings the user selects in real-time, the matching reference value map will be accessed for system dependence compensation by the attenuation coefficient estimator.

The different attenuation coefficient maps produced by the attenuation coefficient estimator are coupled to a confidence measure estimator 52, which produces spatially corresponding maps of estimated confidence (i.e., reliability,) either of a single attenuation coefficient map or of one attenuation coefficient map in relation to another. The attenuation coefficient maps and the results of the confidence estimations are coupled to an attenuation coefficient map compounder 54, which compounds (combines) the coefficient map values in the elevation dimension on a pixel-by-pixel basis, such as by weighted averaging, where the weighting is determined by the confidence estimations. The result is a final attenuation coefficient map produced by not a single estimation method, but from a combination of a plurality of spatially different attenuation coefficient maps. This technique will thus include the benefit of nearby estimates which may be more accurate, e.g., less affected by an in-plane blood vessel, than some of the attenuation coefficient estimates in a given plane of interest. The final attenuation coefficient map is coupled to the scan converter 32 for scan conversion, and then to a graphics processor 44 which formats the map for display, as by color-coding the coefficient values of the map in relation to a range of scaled color values. The attenuation coefficient map is coupled to the display processor 48 for display on the image display 40. Optionally, the confidence estimation maps obtained from confidence measure estimator 52 may be compounded and displayed in the same manner, so that the user can assess the reliability of attenuation estimates made in a particular region of interest (ROI) of the image field. Another way to present attenuation coefficient estimation results is to display only the attenuation image in the central plane (overlapping the echo plane) but use all the attenuation images when calculating average attenuation coefficients. In either display option, the system can allow users to look at attenuation images in different planes during review.

The processor of the attenuation coefficient estimator 50 can use any of a number of techniques for estimating acoustic attenuation coefficient values over an image field, such as the spectral difference method, the spectral log difference method, and the maximum likelihood method. Estimation of acoustic attenuation coefficients (in units of dB/cm or its equivalents) or acoustic attenuation coefficient slope (in units of dB/cm/MHz or its equivalents) from pulse echo signals can be based on the following expressions:

$$S_s(f,z) = P(f)D_s(f,z)A_s(f,z_0)B_s(f,z)\exp[-4\alpha_s(f)(z-z_0)], \quad [1]$$

and $$S_r(f,z) = P(f)D_r(f,z)A_r(f,z_0)B_r(f,z)\exp[-4\alpha_r(f)(z-z_0)], \quad [2]$$

where the subscripts s and r denote tissue sample and reference values, respectively; f is frequency; z is depth in the image field; S(f,z) is a measured power spectrum from a region of interest (ROI) centered at depth z; P(f) is transducer response combined with the spectrum of the transmitted pulses; D(f,z) is diffraction effects; $z_0$ is the starting depth of the ROI; $A(f,z_0)$ is the cumulative attenuation effects from the transducer surface to depth $z_0$; B(f,z) is the effects of acoustic scattering; and $\alpha(f)$ is the attenuation coefficient in the ROI. By using $S_r(f,z)$ from a homogeneous reference phantom and assuming the same speed of sound for the tissue sample and the reference, P(f) and $D_s(f,z)$ are suppressed and the following expression will hold:

$$RS(f,z) \equiv \frac{S_s(f,z)}{S_r(f,z)} \cong \frac{A_s(f,z_0)B_s(f,z)}{A_r(f,z_0)B_r(f)}\exp\{-4(z-z_0)[\alpha_s(f)-\alpha_r(f)]\}. \quad [3]$$

Starting from these relationships, the spectral difference method may be carried out as follows. The spectral difference method assumes that the term $$\frac{A_s(f,z_0)B_s(f,z)}{A_r(f,z_0)B_r(f)}$$

in expression [3] above is independent of z. Accordingly, $$\ln\left[\frac{S_s(f,z)}{S_r(f,z)}\right] \cong -4(z-z_0)[\alpha_s(f)-\alpha_r(f)] + G(f), \quad [4]$$

where $$G(f) = \ln\left[\frac{A_s(f,z_0)B_s(f,z)}{A_r(f,z_0)B_r(f)}\right],$$

and $\alpha_s(f)$ at a given frequency f can be obtained through estimating the slope of $$\ln\left[\frac{S_s(f,z)}{S_r(f,z)}\right]$$

with respect to z. Note that the attenuation coefficient of the reference, $\alpha_r(f)$, is known. In soft tissue α can be modelled as $$\alpha(f) = \beta f^n. \quad [5]$$

When it is assumed that n=1, then $\alpha_r(f)=\beta_r f$, and $\alpha_s(f)=\beta_s f$, and $$\ln\left[\frac{S_s(f,z)}{S_r(f,z)}\right] \cong -4(z-z_0)(\beta_s-\beta_r)f + G(f). \quad [6]$$

The attenuation coefficient slope $\beta_s$ can then be estimated as $$\beta_s \cong \beta_r - \frac{1}{4}\frac{d}{dz}\left(\frac{\int_{f_1}^{f_2}\left[\frac{w(f)}{f}\right]\ln\left[\frac{S_s(f,z)}{S_r(f,z)}\right]df}{\int_{f_1}^{f_2}w(f)df}\right), \quad [7]$$

where w(f) is a weighting function. Note that the effects of G(), assuming the scattering effects $\beta_s$ are independent of depth z, vanish after the differentiation with respect to z. When the assumption of depth independence of scatterers is valid, the spectral difference method usually outperforms other methods such as the maximum likelihood (ML) method. Further detail on the three acoustic attenuation coefficient techniques mentioned above can be found in co-assigned U.S. provisional patent application No. 62/796,372, which is herein incorporated by reference.

In accordance with a further aspect of the present invention, the expressions and assumptions of the attenuation coefficient estimation technique are used to produce spatially corresponding maps of confidence factors of the attenuation coefficient estimates for the coefficient map of each elevationally different plane. Maps of confidence factors for the different attenuation coefficient maps are computed by the confidence measure estimator 52 and used to display the confidence in the attenuation coefficients across the image field, or used to compound the different attenuation coefficient maps in accordance with their trustworthiness. A further option is to compound the confidence factor maps in the elevation dimension, in the same way that the attenuation coefficient maps are compounded. For instance, for the spectral difference method of attenuation coefficient estimation to be valid for accurate coefficient slope estimation, it is necessary for the following expression $$Q(f, z_1, z_2) \equiv \frac{1}{f}\left(\ln\left[\frac{S_s(f, z_2)}{S_r(f, z_2)}\right] - \ln\left[\frac{S_s(f, z_1)}{S_r(f, z_1)}\right]\right) - 4\beta_r \quad [8]$$

to be independent of f. It will be if $$Q(f, z_1, z_2) \cong \hat{Q}(z_1, z_2) \equiv \frac{\int_{f_1}^{f_2} w(f)Q(f, z_1, z_2)df}{\int_{f_1}^{f_2} w(f)df} \quad [9]$$

It can be determined if this is the case by calculating $$u(z_1, z_2) \equiv \frac{\sqrt{\frac{\int_{f_1}^{f_2} w(f)[Q(f, z_1, z_2)\hat{Q}(z_1, z_2)]^2 df}{\int_{f_1}^{f_2} w(f)df}}}{|\hat{Q}(z_1, z_2)|}, \quad [10]$$

The confidence in the coefficient slope estimates is greater when u is smaller and lower when u is larger. A map of u values calculated in this manner for each pixel of an attenuation coefficient map calculated by the spectral difference method thus will inform the user of the trustworthiness of the attenuation coefficient map and the accuracy of coefficient estimations for the points throughout the attenuation coefficient map. Differences between a raw attenuation coefficient map and its smoothed version (e.g., one which has undergone median filtering) can also be used to indicate confidence, with higher confidence values assigned to pixels with lower differences. Other methods or metrics for deriving confidence measures include texture analysis, flow measurement, tissue response to acoustic radiation force, and coherence in pre-beam-summed channel data.

The attenuation coefficient map compounder 54 produces a final attenuation coefficient map by compounding the elevationally different attenuation coefficient maps. During compounding, the coefficient values of an attenuation coefficient map with higher confidence factors and/or higher consistency with other maps will be given larger weights in the combining process. For instance, if an attenuation coefficient from one map for a given pixel has a higher confidence factor than the coefficients from the other maps, that coefficient value will be given greater weight than the others in the combining process. If the attenuation coefficients from two of the maps have a higher consistency than the attenuation coefficient from a third map, e.g., are within 5% of each other, whereas the value from the third map differs by 20% from the others, then the coefficients from the first two maps would be given greater weights in the combining process. Compounding of the different maps proceeds in this manner in the elevation dimension on a pixel-by-pixel basis until a final attenuation map has been produced for display to the user. As previously mentioned, the final map can be displayed alone, or in conjunction with one or all of the confidence maps or, preferably, in conjunction with a consolidated confidence map.

Figure 2:
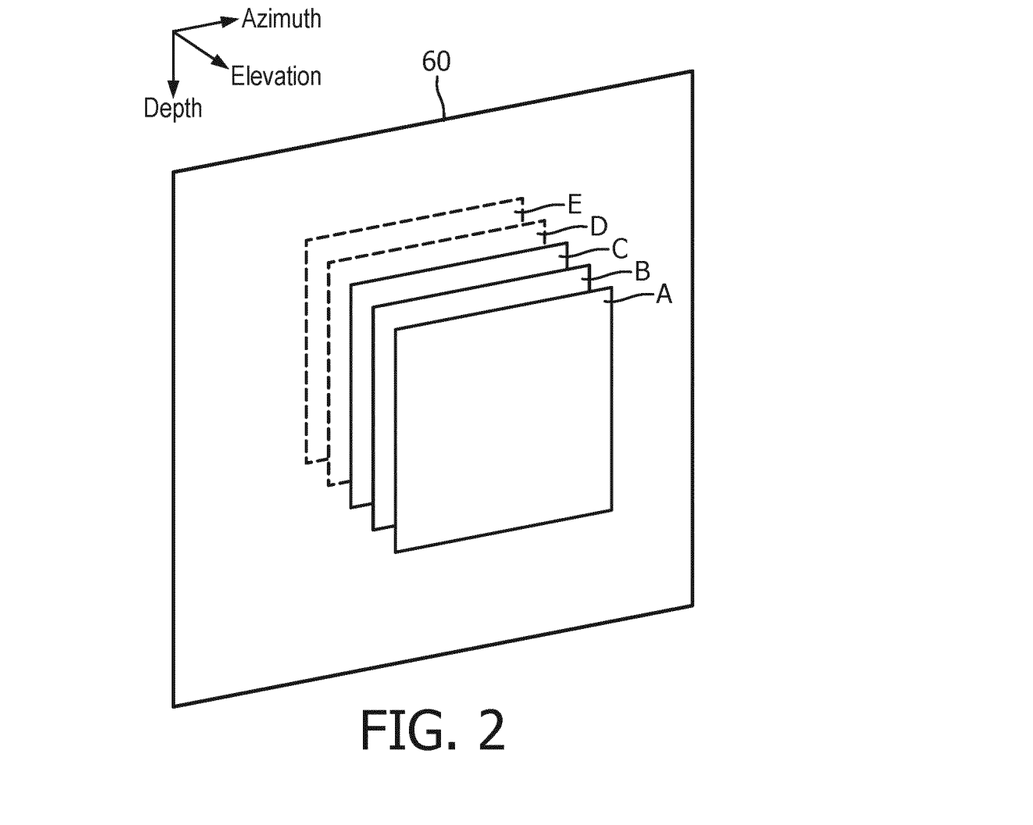
FIG. 2 illustrates a perspective view of the plane of a guidance image and several elevationally differing regions where acoustic attenuation coefficients are estimated for subsequent compounding.
Figure 2A:
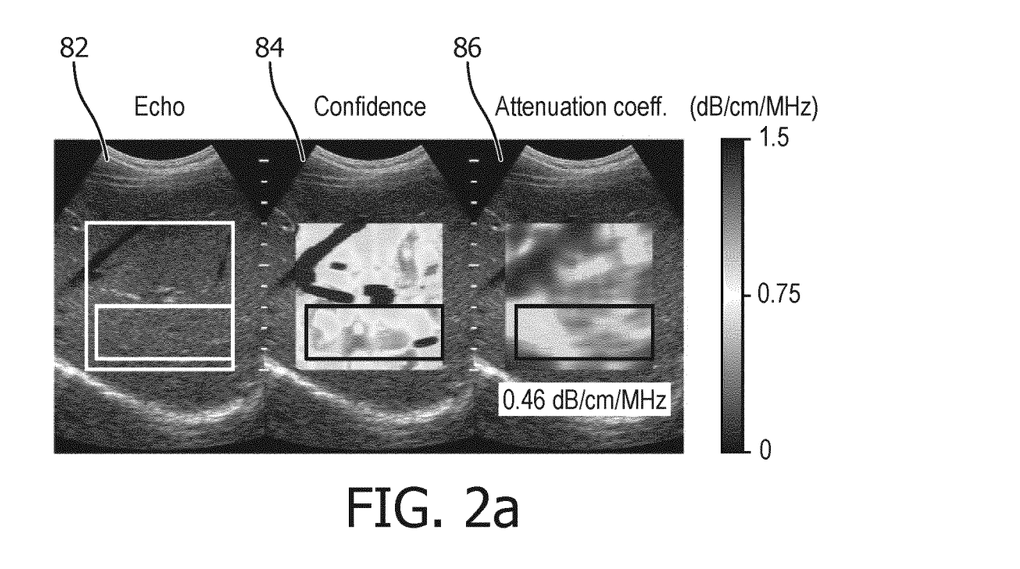
FIG. 2*a* illustrates a guidance image with a region of interest containing an anatomically registered acoustic attenuation coefficient map.

FIG. 2 is a perspective view of the elevation compounding technique of the present invention. The plane 60 is the plane of an ultrasound image acquired for image guidance of the procedure. Located in correspondence with this image plane are elevationally different planes A, B, C, D and E from which echo signals are acquired for the computation of acoustic attenuation coefficient values in each plane. The plane C is in the plane of the guidance image plane 60 and defines a region of interest in the plane 60 for acoustic attenuation estimation. Planes A and B are in front of plane 60 in the elevation dimension and planes D and E are behind the plane 60. After an acoustic attenuation coefficient map has been computed for each of the five planes using the expressions given above, the five acoustic attenuation maps are compounded pixel-by-pixel in the elevation direction to produce a compound acoustic attenuation map of the region of interest in plane 60. The compounding may be performed with or without confidence weighting as described above. FIG. 2a illustrates three image panels formed in accordance with the present invention, an image panel 82 displaying an echo image with a designated ROI, an image panel 86 with the ROI illustrating color-coded attenuation coefficient values, and an image panel 84 with confidence factors color-coded in the ROI.

Figure 3:
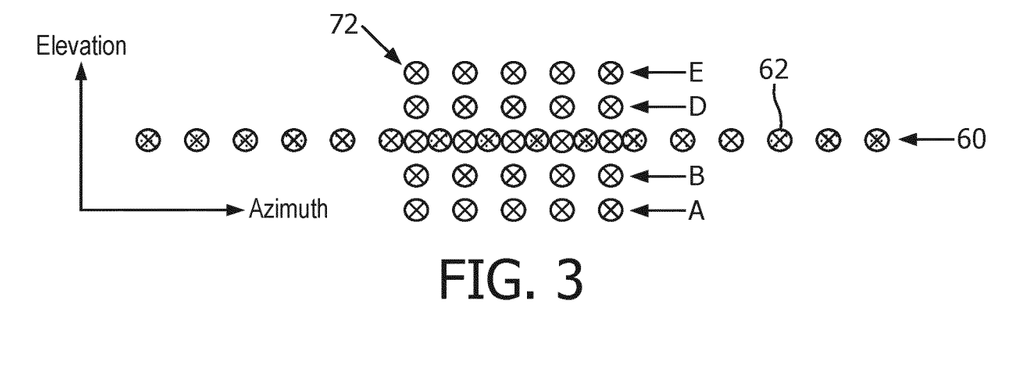
FIG. 3 is an axial view of ultrasound beams used to scan the guidance image and planes for acoustic attenuation estimation shown in FIG. 2.

FIG. 3 is an axial view from the transducer array of some of the beams used to acquire echo signal data for the guidance image and the compounded acoustic attenuation mapping shown in FIG. 2. The beams 62 in the plane 60 are used to acquire echo signals for the guidance image, and the beams 72 are used to acquire echo signals for acoustic attenuation coefficient maps in the five elevationally separated planes A-E. The echo signal data from the acoustic attenuation mapping planes A-E may be acquired one plane at a time and coupled to the attenuation coefficient estimator 50 for the computation of an attenuation coefficient map for one plane before the echo signal data for another attenuation coefficient map plane is acquired, using either a 1.75D or 2D array transducer. When a 2D array transducer with full electronic steering in the elevation dimension is used in the multi-line mode, as described in U.S. Pat. No. 8,137,272 (Cooley et al.), echoes along a scanline of each elevation plane may be acquired at the same time in response to a single pulse transmission. Transmission and reception proceeds in this manner, enabling all of the different elevational planes to be acquired in the same time needed to scan a single plane with a 1D array by virtue of the use of multi-line acquisition. After all of the echo signals for all of the planes have been acquired in this way, the different elevation plane acoustic attenuation maps are calculated by the attenuation coefficient estimator 50 then compounded by the attenuation coefficient map compounder for production of the final attenuation coefficient map of the ROI.

The location of transmits for attenuation imaging can vary from volume to volume and does not need to stay on a regular grid in the lateral-elevational plane.

Figure 4:
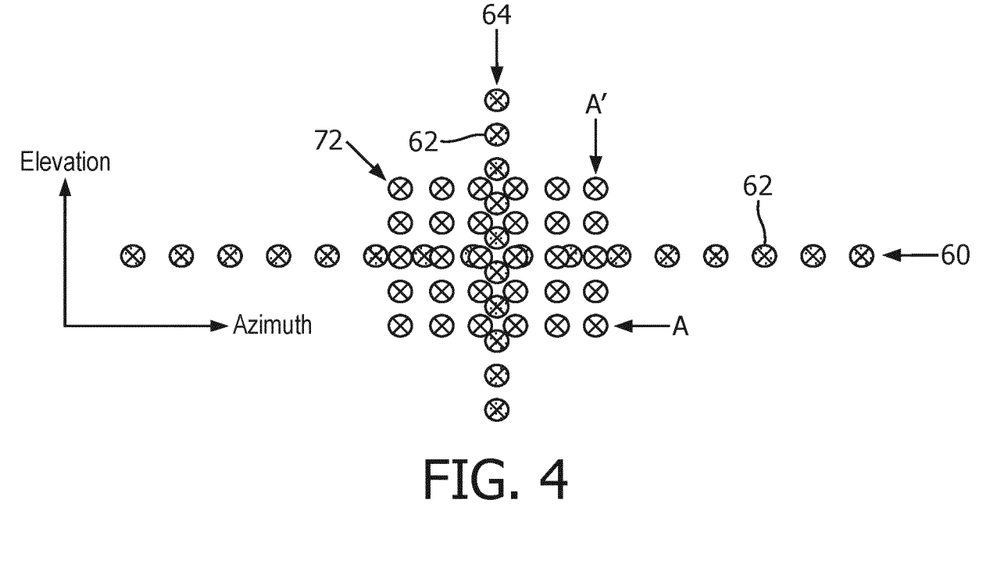
FIG. 4 is an axial view of ultrasound beams used to scan two orthogonal guidance images and to scan elevationally separated planes for acoustic attenuation compounding in either of the guidance image planes.

FIG. 4 illustrates another implementation of the present invention using a 2D array to acquire two orthogonal guidance images, one in plane 60 and the other in orthogonal direction 64. The echo signal data for the attenuation coefficient map planes is acquired along beams 72 as described above. This echo signal data may be processed in one of two ways, either by processing rows of echo signals (A) for the production of attenuation coefficient maps in the elevation dimension as described in FIG. 3, or by producing attenuation coefficient maps for columns (A') of echo signals to produce a compounded attenuation coefficient map for an ROI in the orthogonal guidance image of plane 64. In the latter case, the elevation and azimuth dimensions are reversed for the orthogonal guidance image of plane 64 and its attenuation coefficient map. The user may switch back and forth between the two guidance images of planes 60 and 64 and their attenuation coefficient maps, or display both at the same time.

Figure 5:
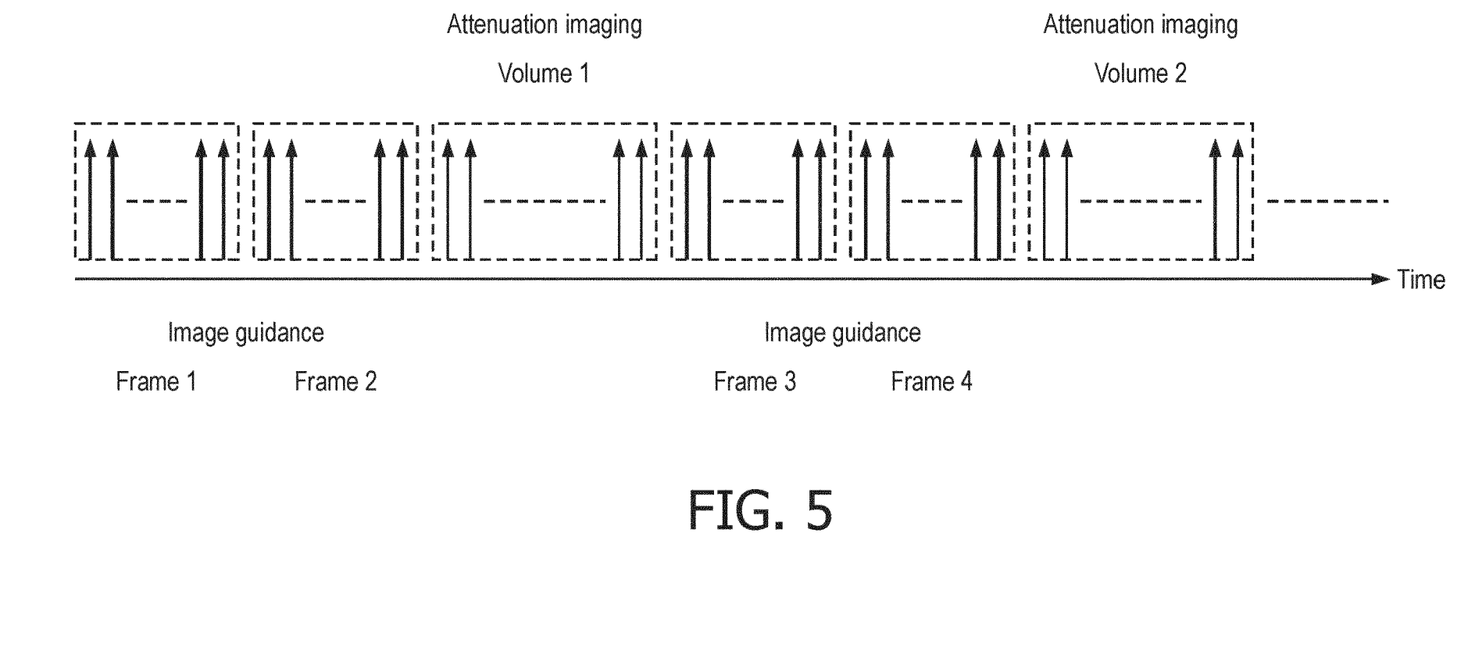
FIG. 5 illustrates the time-interleaving of guidance image acquisition and the acquisition of echo signal data for acoustic attenuation estimation.

A timing diagram for acquiring the echo signal data from the guidance planes and for the attenuation coefficient maps of FIG. 4 is shown in FIG. 5. As the timing diagram illustrates, the scanning of the image guidance planes is alternated with the acquisition of echo signal data for the attenuation coefficient maps. Initially Frame 1 (plane 60) and then Frame 2 (Plane 64) are scanned and guidance images are produced from the two frames of echo signal data. Then Volume 1 is scanned with beams 72 to acquire a volume of echo signal data for the attenuation coefficient maps. As explained above, this data can be processed in planes in one direction to produce elevationally different attenuation coefficient maps for one of the guidance images, and/or in an orthogonal direction to produce elevationally different attenuation coefficient maps for the other, orthogonal guidance image. The scanning sequence then continues in this manner, updating the guidance images with echo signals from Frame 3 and Frame 4, then updating the attenuation coefficient maps by processing echo signal data from the acquisition of Volume 2 echo signals.

Figure 6:
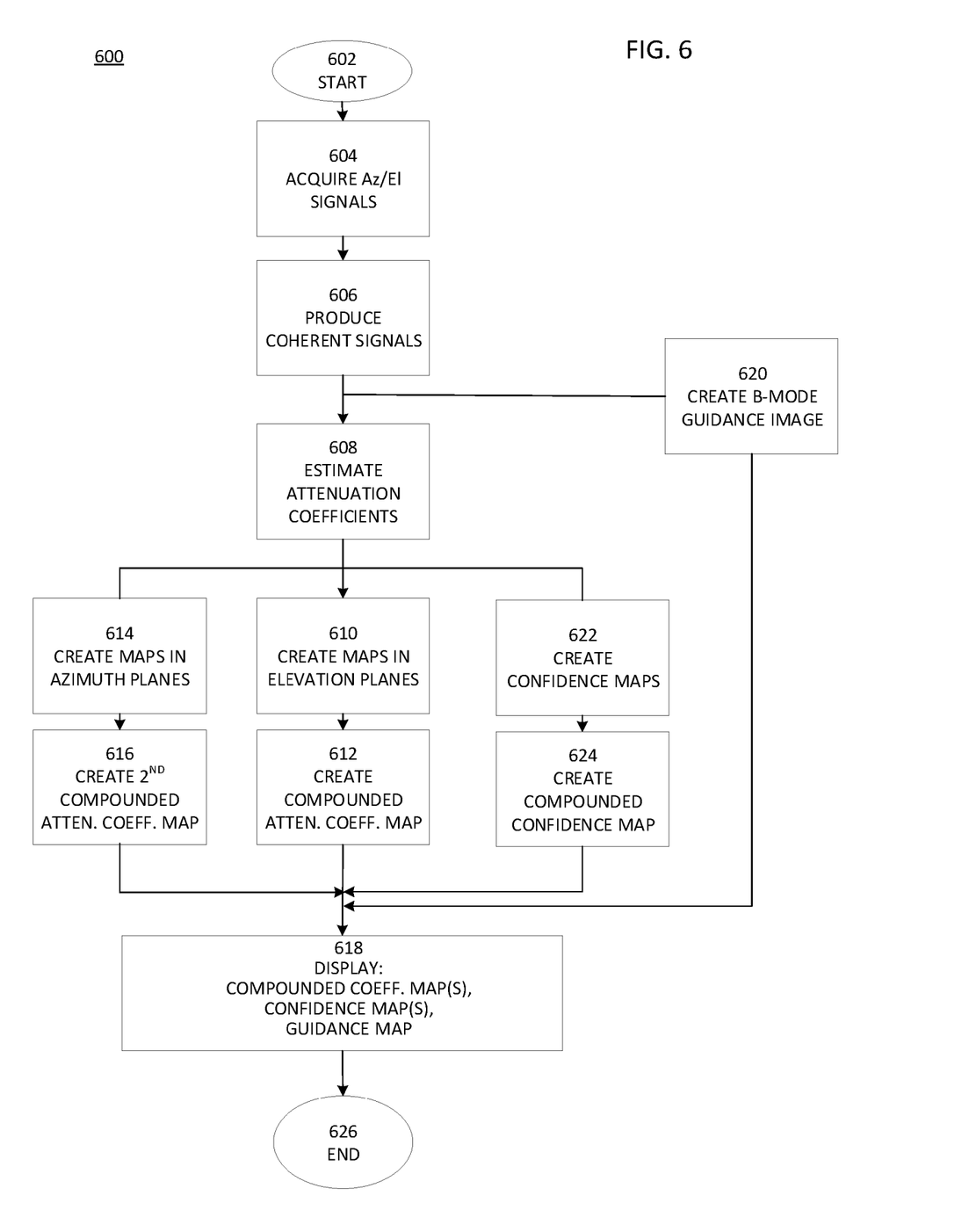
FIG. 6 is a flow chart of methods for creating and displaying a compounded attenuation coefficient map.

FIG. 6 illustrates a method flow chart of a method 600 for automatically producing an attenuation coefficient map in an ultrasound image field. The method generally incorporates the functions and features of the afore-described ultrasonic diagnostic imaging system and as shown in FIGS. 1 through 5. Method 600 begins at start step 602, e.g. with obtaining and initializing a system for acquiring ultrasound echo signals. Ultrasound echo signals from an image field are received in an acquiring step 604, with signals preferably acquired in both azimuth and elevation dimensions. The system produces coherent echo signals at producing step 606 from the raw received signals from acquiring step 604. An estimating step 608 then estimates attenuation coefficient values based upon the coherent echo signals. Optionally, a B-mode guidance image may also be derived from the coherent echo signals produced at step 606 in a B-mode image create step 620.

The system uses the attenuation coefficients from estimating step 608 to automatically create attenuation coefficient maps at create step 610. Maps are created for at least two elevation planes, although the invention envisions creating maps for greater than two planes. Then, according to the techniques described previously, the system compounds the two or more attenuation maps at step 612 to obtain a compounded attenuation coefficient map. The advantages of the compounded attenuation coefficient map are described previous as well.

The obtained compounded attenuation map from step 612 may then be used for various purposes, including further analysis, or automatic adjustment of system settings. A display step 618, for example, may also provide a visual display of the obtained compounded attenuation coefficient map. In an optional embodiment, the B-mode guidance image created at step 620 may be displayed at step 618 along with the compounded attenuation coefficient map in, for example, anatomical registration with a region of interest of the guidance image.

A second compounded attenuation coefficient map may also be obtained from a plurality of planes in different orientations from the elevation planes. For example, step 614 automatically creates a plurality of such attenuation coefficient maps of attenuation coefficient values in the azimuth dimension. The azimuth dimension is of course orthogonal to the elevation dimension, but other angular orientations fall within the scope of the invention. Then, according to the techniques described previously, the system compounds the two or more attenuation maps at step 616 to obtain a second compounded attenuation coefficient map in the different plane.

The second compounded attenuation map from step 616 may then be used for various purposes, including further analysis, or automatic adjustment of system settings. The second compounded attenuation map may be displayed at display step 618, or may be displayed along with the compounded attenuation coefficient map from step 612.

Optionally, a plurality of confidence factor maps of attenuation coefficients, corresponding to different planes, may be created at creating step 622. The confidence maps preferably correspond to the values associated with the attenuation coefficient maps created in step 610 or step 614. The plurality of maps may then be used to create a compounded confidence map of attenuation coefficients at create step 624. Each compounded confidence value there is preferably associated with a corresponding compounded attenuation coefficient value. The compounded confidence factor map may be displayed at display step 618, an may be displayed along with the compounded attenuation coefficient map from step 612 or step 616.

It should be noted that an ultrasound system suitable for use in an implementation of the present invention, and in particular the component structure of the ultrasound system of FIG. 1, may be implemented in hardware, software or a combination thereof. The various embodiments and/or components of an ultrasound system and its controller, or components and controllers therein, also may be implemented as part of one or more computers or microprocessors. The computer or processor may include a computing device, an input device, a display unit and an interface, for example, for accessing the internet. The computer or processor may include a microprocessor. The microprocessor may be connected to a communication bus, for example, to access a PACS system or the data network for importing training images. The computer or processor may also include a memory. The memory devices such as a memory for the reference value map for the attenuation coefficient estimator 50 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine. The set of instructions of an ultrasound system including those controlling the acquisition, processing, and display of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. The equations given above for the different methods for attenuation coefficient estimation and mapping, as well as the calculations used to produce the confidence maps described above, are typically calculated by or under the direction of software routines. Further, the software may be in the form of a collection of separate programs or modules such as an attenuation coefficient computing module, or an attenuation coefficient mapping program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound imaging system which produces attenuation coefficient maps of an image field comprising:
    an ultrasound probe with a 1.75D or 2D transducer array adapted to acquire ultrasonic echo signals from the image field in the azimuth and elevation dimensions;
    a beamformer adapted to process the ultrasonic echo signals to produce coherent echo signals for an ultrasound image of the image field;
    an attenuation coefficient estimator, coupled to the beamformer, and adapted to estimate attenuation coefficient values for maps of attenuation coefficients,
    wherein the attenuation coefficient estimator is further adapted to produce a plurality of attenuation coefficient maps in different planes in the elevation dimension;
    a confidence factor estimator, responsive to attenuation coefficient map data, which is adapted to produce a map of confidence factors pertaining to corresponding values of the attenuation coefficient map;
    an attenuation coefficient map compounder, coupled to the attenuation coefficient estimator, and adapted to compound the plurality of attenuation coefficient maps in the elevation direction; and
    a display adapted to display attenuation coefficient maps produced by the attenuation coefficient map compounder.

2. The ultrasound imaging system of claim 1, wherein the attenuation coefficient map compounder is further adapted to compound two or more of the attenuation coefficient maps produced by the attenuation coefficient estimator on a pixel-by-pixel basis in the elevation direction.

3. The ultrasound imaging system of claim 1, wherein the attenuation coefficient map compounder is further adapted to compound two or more of the attenuation coefficient maps using weights determined by confidence factor estimations.

4. The ultrasound imaging system of claim 1, further comprising a memory adapted to store a map of reference values,
    wherein the reference values comprise attenuation coefficient measurements of a tissue phantom, a theoretical model of attenuation coefficients, or a numerical simulation of attenuation coefficients.

5. The ultrasound imaging system of claim 1, further comprising a B mode processor, coupled to receive the coherent echo signals and adapted to produce B mode image signals for the attenuation coefficient estimator.

6. The ultrasound imaging system of claim 5, wherein the attenuation coefficient estimator is further adapted to estimate attenuation coefficient values by the spectral difference method, the spectral log difference method, or the maximum likelihood method.

7. The ultrasound imaging system of claim 5, wherein the B mode processor is further adapted to produce echo signals for a guidance image,
    wherein a compounded attenuation coefficient map produced by the attenuation coefficient map compounder is in anatomical registration with a region of interest of the guidance image.

8. The ultrasound imaging system of claim 1, wherein the attenuation coefficient map compounder is further adapted to compound two or more of the attenuation coefficient maps produced by the attenuation coefficient estimator by weighted averaging.

9. The ultrasound imaging system of claim 8, wherein the attenuation coefficient map compounder is further adapted to compound two or more of the attenuation coefficient maps using weights determined by attenuation coefficient consistency of the maps being compounded.

10. The ultrasound imaging system of claim 1, wherein the transducer array is a 2D array adapted to simultaneously acquire ultrasonic echo signals for a plurality of elevationally different attenuation coefficient maps by multi-line acquisition.

11. The ultrasound imaging system of claim 10, wherein the beamformer is further adapted to produce coherent echo signals for two orthogonal ultrasound images.

12. The ultrasound imaging system of claim 11, wherein the transducer array is further adapted to alternately acquire echo signal data for ultrasound images and echo signal data for attenuation coefficient mapping in a time-interleaved manner.

13. The ultrasound imaging system of claim 11, wherein the attenuation coefficient estimator is further adapted to estimate attenuation coefficient values for maps of attenuation coefficients in either the azimuth or the elevation dimensions.

14. The ultrasound imaging system of claim 13, wherein the attenuation coefficient map compounder is further adapted to compound a plurality of attenuation coefficient maps in the elevation direction of two orthogonally oriented ultrasound images.

15. A method for automatically producing an attenuation coefficient map in an ultrasound image field, comprising the steps of:

acquiring ultrasound echo signals from the ultrasound image field in the azimuth and elevation dimensions;

producing coherent echo signals from the ultrasound echo signals;

estimating attenuation coefficient values corresponding to the coherent echo signals;

automatically creating a plurality of attenuation coefficient maps for attenuation coefficient values in a plurality of different planes in the elevation dimension;

estimating confidence factor, responsive to attenuation coefficient map data, to produce a map of confidence factors pertaining to corresponding values of the attenuation coefficient map;

compounding the plurality of attenuation coefficient maps to obtain a compounded attenuation coefficient map; and displaying the compounded attenuation coefficient map.

16. The method of claim 15, further comprising the steps of:

creating a B mode ultrasound guidance image from the coherent echo signals; and displaying the B mode ultrasound image and compounded attenuation coefficient map in anatomical registration with a region of interest of the guidance image.

17. The method of claim 15, further comprising the steps of:

automatically creating a plurality of attenuation coefficient maps for attenuation coefficient values in a plurality of different planes in the azimuth dimension;

compounding the plurality of attenuation coefficient maps, for attenuation coefficient values in the plurality of different planes in the azimuth dimension, to obtain a second compounded attenuation coefficient map in a different plane than of the compounded attenuation coefficient map; and displaying at least one of the compounded attenuation coefficient map and the second compounded attenuation coefficient map.

18. A non-transitory computer-readable medium containing instructions that in response to execution on a processor connected to the computer-readable medium, implement the method of claim 15.

* * * * *